(12) United States Patent
Bublitz et al.

(10) Patent No.: US 9,456,746 B2
(45) Date of Patent: Oct. 4, 2016

(54) SYSTEMS AND METHODS FOR BROAD LINE FUNDUS IMAGING

(71) Applicant: Carl Zeiss Meditec, Inc., Dublin, CA (US)

(72) Inventors: Daniel Bublitz, Rausdorf (DE); Matthew J. Everett, Livermore, CA (US); Csaba Farkas, Pleasanton, CA (US); Michael Kempe, Jena (DE); Yue Qiu, Pleasanton, CA (US); Tobias Schmitt-Manderbach, Jena (DE)

(73) Assignees: CARL ZEISS MEDITEC, INC., Dublin, CA (US); CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 14/207,229

(22) Filed: Mar. 12, 2014

(65) Prior Publication Data
US 2015/0131050 A1    May 14, 2015

Related U.S. Application Data

(60) Provisional application No. 61/799,257, filed on Mar. 15, 2013.

(51) Int. Cl.
*A61B 3/00* (2006.01)
*A61B 3/14* (2006.01)
*A61B 3/10* (2006.01)
*G02B 21/00* (2006.01)
*A61B 3/12* (2006.01)

(52) U.S. Cl.
CPC ............ *A61B 3/14* (2013.01); *A61B 3/1025* (2013.01); *A61B 3/12* (2013.01); *G02B 21/0028* (2013.01); *G02B 21/0032* (2013.01)

(58) Field of Classification Search
USPC .......................................................... 351/249
See application file for complete search history.

(56) References Cited

U.S. PATENT DOCUMENTS

| 3,547,512 A | 12/1970 | Baer |
| 4,135,791 A | 1/1979 | Govignon |
| 4,170,398 A | 10/1979 | Koester |

(Continued)

FOREIGN PATENT DOCUMENTS

| DE | 102011053880 A1 | 3/2013 |
| EP | 2338407 A1 | 6/2011 |

(Continued)

OTHER PUBLICATIONS

International Search Report and Written Opinion received for PCT Patent Application No. PCT/EP2014/055076, mailed on Oct. 13, 2014, 22 pages.

(Continued)

*Primary Examiner* — Jack Dinh
(74) *Attorney, Agent, or Firm* — Morrison & Foerster LLP

(57) ABSTRACT

Systems and methods for Broad Line Fundus Imaging (BLFI), an imaging approach that is a hybrid between confocal and widefield imaging systems, are presented. These systems and methods are focused on improving the quality and signal of broad line fundus images or imaging methods to create high contrast and high resolution fundus images. Embodiments related to improved pupil splitting, artifact removal, reflex minimization, adaptable field of view, instrument alignment and illumination details are considered.

11 Claims, 11 Drawing Sheets

(56) References Cited

U.S. PATENT DOCUMENTS

| | | |
|---|---|---|
| 4,400,070 A | 8/1983 | Isono et al. |
| 4,478,482 A | 10/1984 | Koester |
| 4,732,466 A | 3/1988 | Humphrey |
| 4,768,874 A | 9/1988 | Webb et al. |
| 4,838,679 A | 6/1989 | Bille |
| 4,854,692 A | 8/1989 | Kobayashi |
| 4,991,953 A | 2/1991 | Pflibsen et al. |
| 5,028,802 A | 7/1991 | Webb et al. |
| 5,177,511 A | 1/1993 | Feuerstein et al. |
| 5,239,178 A | 8/1993 | Derndinger et al. |
| 5,757,463 A | 5/1998 | Kohayakawa |
| 5,784,148 A | 7/1998 | Heacock |
| 5,861,939 A | 1/1999 | Heacock |
| 5,984,474 A | 11/1999 | Schweitzer et al. |
| 6,236,877 B1 | 5/2001 | Elsner et al. |
| 6,267,477 B1 | 7/2001 | Karpol et al. |
| 6,640,124 B2 | 10/2003 | Elsner et al. |
| 7,284,859 B2 | 10/2007 | Ferguson |
| 7,292,390 B2 | 11/2007 | Lin et al. |
| 7,331,669 B2 | 2/2008 | Elsner |
| 7,335,898 B2 | 2/2008 | Donders et al. |
| 7,477,380 B2 | 1/2009 | Knebel et al. |
| 7,567,726 B2 | 7/2009 | Westphal |
| 7,586,086 B2 | 9/2009 | Lauer |
| 7,648,242 B2 | 1/2010 | Ferguson et al. |
| 7,706,584 B2 | 4/2010 | Saggau et al. |
| 7,831,106 B2 | 11/2010 | Elsner et al. |
| 7,854,510 B2 | 12/2010 | Verdooner et al. |
| 8,100,531 B2 | 1/2012 | Liesfeld et al. |
| 8,237,835 B1 | 8/2012 | Muller et al. |
| 8,488,895 B2 | 7/2013 | Muller et al. |
| 8,714,743 B2 | 5/2014 | Verdooner et al. |
| 8,814,362 B2 | 8/2014 | Verdooner et al. |
| 2005/0254008 A1 | 11/2005 | Ferguson et al. |
| 2006/0228011 A1 | 10/2006 | Everett et al. |
| 2007/0031002 A1 | 2/2007 | Venkatesh et al. |
| 2007/0291277 A1 | 12/2007 | Everett et al. |
| 2010/0128221 A1 | 5/2010 | Muller et al. |
| 2012/0249956 A1 | 10/2012 | Narasimha-Iyer et al. |
| 2013/0222763 A1 | 8/2013 | Bublitz et al. |
| 2014/0232987 A1 | 8/2014 | Westphal et al. |

FOREIGN PATENT DOCUMENTS

| | | |
|---|---|---|
| JP | 6-7301 A | 1/1994 |
| WO | 2012/059236 A1 | 5/2012 |

OTHER PUBLICATIONS

Poher et al., "Improved Sectioning in a Slit Scanning Confocal Microscope", Optics Letters, vol. 33, No. 16, Aug. 15, 2008, pp. 1813-1815.

Invitation to Pay Additional Fees received for PCT Patent Application No. PCT/EP2014/055076, mailed on Jul. 25, 2014, 8 pages.

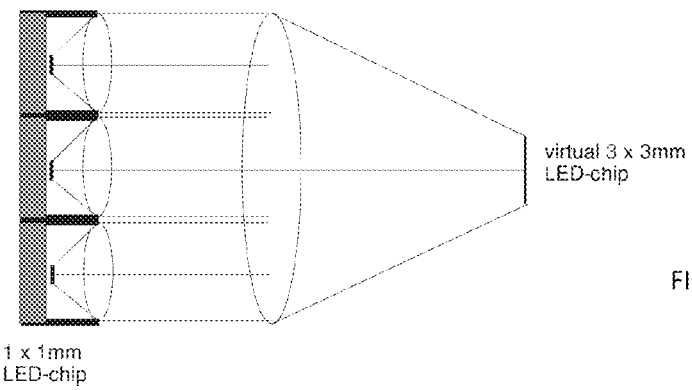
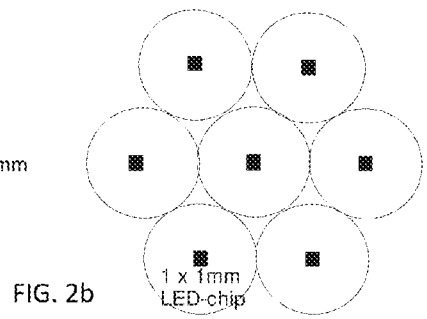
FIG. 2b
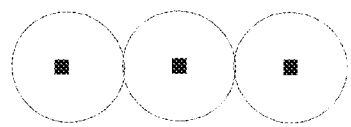
FIG. 2a
FIG. 2c
FIG. 2
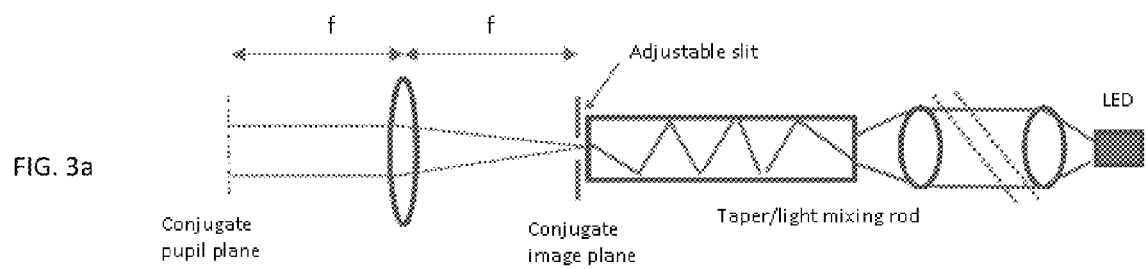
FIG. 3a
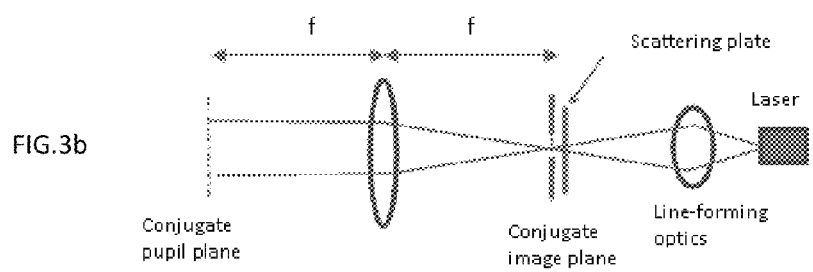
FIG. 3b

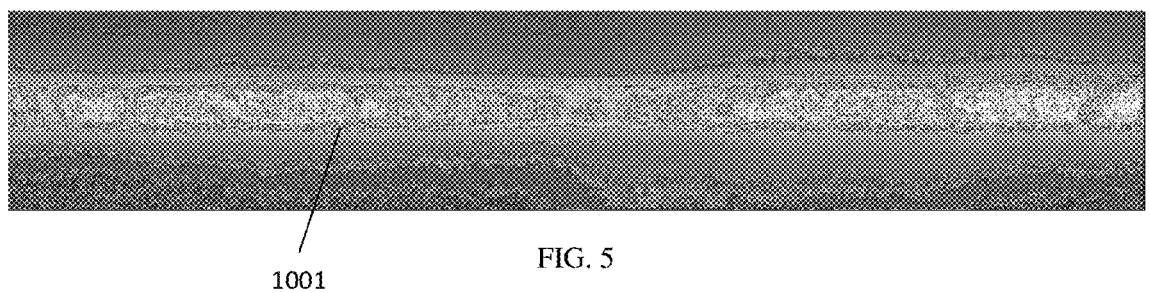
1001  FIG. 5
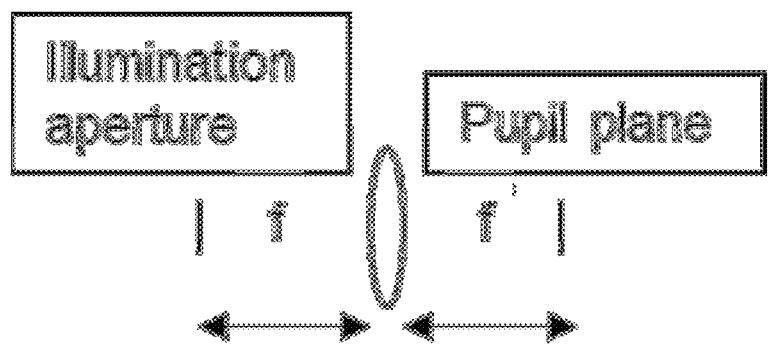
FIG. 6

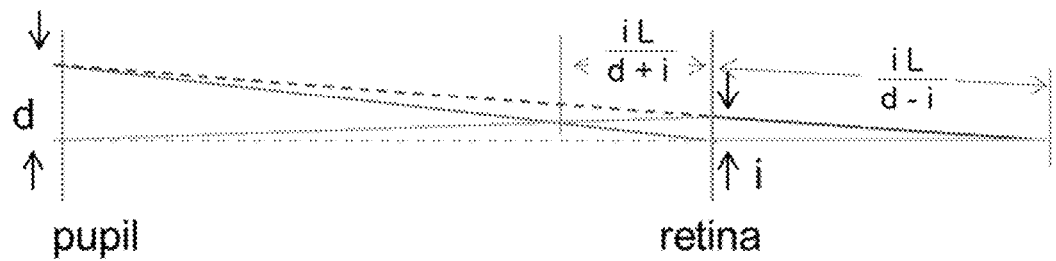
Fig. 12
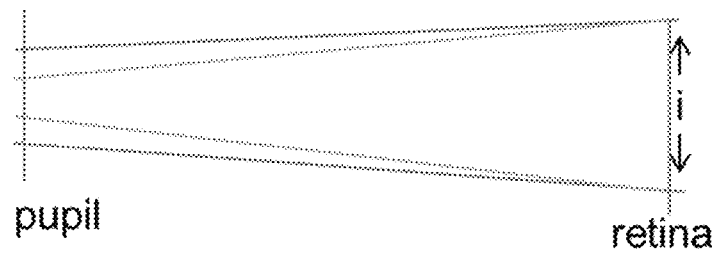
Fig. 13a
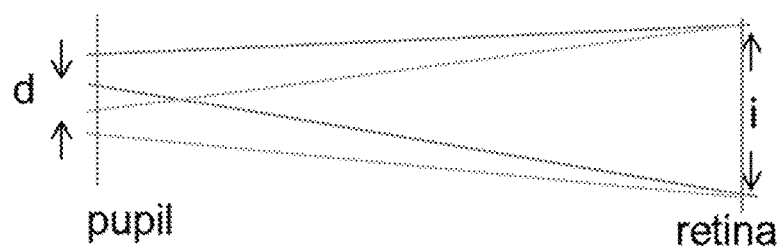
Fig. 13b
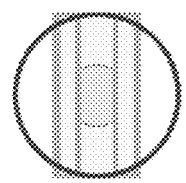 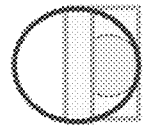
Large pupil    Small pupil
FIG. 14

SYSTEMS AND METHODS FOR BROAD LINE FUNDUS IMAGING

PRIORITY

The present application claims priority to U.S. Provisional Application Ser. No. 61/799,257 filed Mar. 15, 2013, the contents of which are hereby incorporated in its entirety by reference.

TECHNICAL FIELD

This application is related to the field of fundus imaging, in particular improved systems and methods for broad line fundus imaging.

BACKGROUND

A variety of imaging modalities have been applied to generating images of the retina or fundus of the eye. Two well established techniques are widefield imaging typically accomplished by classic fundus cameras and confocal scanning laser ophthalmoscope (cSLO) imaging designs. Fundus cameras illuminate large fields of the retina typically with a flash lamp and take still photos with a two-dimensional camera. To avoid detecting specular reflections of the illumination light at the cornea, a ring-shaped mirror reflects the illumination light to the eye creating an annular aperture near the cornea, which does not overlap with the central disc like aperture which is used for detection. Thus a separation of the illumination and detection path near the cornea is realized, which is known as aperture or pupil splitting. To prevent specular reflections of the illumination light at optical surfaces of the fundus camera itself, especially from the ophthalmic lens, from being detected by the camera, so called dark spots in the illumination path prevent that specific surface area of the optics from being illuminated. Fundus cameras have the advantage that taking images of the retina is fast, thus for example no movement artifacts are observed, and they realize a high lateral resolution with high signal level and dynamic range.

Widefield imaging systems such as fundus cameras have the following limitations:

1. They collect light from all depths within the eye, leading to issues with contrast and reflexes. Thus the contrast in fundus images can be low, which is especially observed in eyes having cataracts.
2. The need to eliminate reflexes puts strict constraints on the system, limiting the field of view to roughly 60 degrees, and making it difficult to combine with other modalities.
3. Finally, the full field of view of the imaging system is used simultaneously, eliminating the option of dynamic adaptive optics for image enhancement.

Another concept of imaging the retina is realized by point confocal scanning systems. These systems image the fundus by illuminating a small spot of the retina with a laser and detecting the reflected or emitted light (e.g. in case for fluorescence modes) by a detector with a pinhole in front of the detector. This pinhole is optically conjugated to the illuminated spot on the retina. Due to the confocal arrangement of illumination and detection, stray-light and out of focus light is suppressed. For imaging the retina the spot is laterally scanned. Confocal scanners have the advantage of suppressing out of focus light, thus showing high contrast images.

Point scanning confocal imaging systems such as a cSLO have the following limitations:

1. They operate with point illumination, requiring the use of lasers or SLDs, which are expensive, and creating a high instantaneous intensity on the eye, making safety more challenging.
2. As each point is imaged sequentially, they require fast transverse scanning to avoid motion artifacts, which is expensive, and may require resonant scanners, which limit imaging flexibility.
3. It can be difficult to achieve enough confocality to completely eliminate the eye reflex, and such a confocal system causes structures such as the optic disk to appear dark because they are not in the plane of the retina.

Another concept for imaging the retina is realized in line scanning systems. In contrast to point confocal systems a line instead of a point is illuminated by a laser and detected at a camera. These systems maintain confocal suppression of out of focus light perpendicular to the line but lack the confocal suppression along the line. The line width in detection can be adapted to the amount of suppression of out of focus light that is necessary. Line scanning has been combined with aperture splitting known from classical fundus imaging (see for example Muller et al. US Patent Publication No. 2010/0128221) and also with ellipsiodal modifications of the illumination pupil to avoid vignetting and to get a uniformly illuminated line at the retina. Muller et al. also discloses so called non-de-scanned or imaged systems, where the scanning over the retina is realized only in illuminating or scanning line illumination over the retina and scanning line detection over the retina is realized by different mechanisms.

The advantage of the line scanning system according to Muller is that it can scan faster across the retina, thus being less sensitive to motion artifacts, but at the expense of less out of focus suppression. But still motion artifacts are observed and lateral resolution and dynamic range is limited compared to fundus cameras. In addition often contrast is also limited because stray-light even coming from areas perpendicular to the line is still present in the detected signal.

Line scanning also creates new problems:

1. Variations in line intensity or linear array sensitivity lead to streaking in the image.
2. Confocality is reduced, requiring a mask to eliminate the eye reflex. This mask compromises the optical efficiency of the system, leading to dim images.

Another concept of imaging the retina is the broad line scanner and method described in WO2012059236 by Bublitz. Bublitz discloses basic elements of a broad line fundus imager (BLFI) and methods. Bublitz further discloses the usage of LED sources with higher etendues than lasers, which is possible in contrast to a classical line scanner because the field of a broad line illumination is significantly wider than the line of a confocal line scanner. Bublitz further discloses that camera locations whose corresponding locations on the retina are not illuminated can be detected to evaluate background or stray light levels coming from out of focus region of the eye. This background is then subtracted from the image of the illuminated broad line. Bublitz also discloses a different pupil splitting for illumination and detection near the cornea than is typical for fundus cameras: instead of illumination of an annular ring, a slit is illuminated, and the detection is done via two caps of a disc at the periphery of the aperture. In addition, the orientation of the illumination slit is perpendicular to the illumination line at the retina.

Bublitz discloses a non-de-scanned detection setup using an electronic or rolling shutter camera with activated camera lines, when the corresponding line of the fundus is illuminated by the broad line or when background level is measured, but as described by German Patent Application No. DE 10 2011 053 880.1 also a de-scanned detection scheme allowing for continuous scanning can be used.

The advantage of the designs disclosed by Bublitz is that for each of the line images the benefits of classical fundus cameras are achieved: long integration times due to broad line illumination, high dynamic range, high lateral resolution due to broad line image being 2D-sampled by a high resolution 2D-camera, usage of classical light sources or LEDs having a broader wavelength spectra than lasers. Also due to faster scans, motion artifacts are reduced. In addition, a significant reduction in sensitivity to stray light by not illuminating the whole retina and measurement of background/stray light level and subtraction can be achieved. Thus the images show better contrast. But experiments have shown that further improvements are necessary to get result comparable to confocal scanners. In addition, motion artifacts still occur, due to each line of the camera having its unique illumination time window, when the data for that specific camera line is detected.

SUMMARY

Here, we propose improved systems and methods for Broad Line Fundus Imaging (BLFI), an imaging approach that is a hybrid between confocal and widefield systems. These hybrid designs have the potential to create high contrast fundus images using low cost light sources (LEDs) with resolution similar to a classic fundus camera. The term broad is used herein to distinguish from classic line scanning systems where the beam is focused to a line limited by diffraction and optical aberrations and the source is typically a laser or a superluminescent diode (SLD).

The broad line fundus imaging (BLFI) scanning system design comprises the following elements:
1. Stepping or scanning of a small region of illumination across the eye so as to generate an image of the full area of interest. A first aperture, confocal to this illumination, collects the light from the retina to generate a "bright image". This aperture limits stray and reflex light from other planes to a manageable level, but need not be small enough to eliminate it.
2. Optional acquisition and subtraction of a "dark image" to remove the unwanted stray and scattered light so as to generate a high contrast reflex free image.
3. If scattering and reflexes from the eye are an issue, this dark image can be acquired through a second aperture, slightly misaligned to the illumination, that collects the limited stray and reflex light, but does not collect image light. Depending on the design, acquisition through this second aperture can be either simultaneous with or sequential to collection through the first aperture. Note that it may be important to acquire dark images for color imaging in the presence of a cataract, where there will be additional out of focus scattering.
4. Further, to reduce or eliminate reflexes from the lenses of the acquisition system, a "no-eye" image without the object can be acquired prior to the image acquisition, potentially during manufacture of the instrument.

The key advantages of such a hybrid system are as follows:

1. As multiple pixels are acquired simultaneously, a high (compared to a laser) etendue light source such as an LED can be used, and high pixel count images can be generated.
2. This makes a low cost imaging system possible, with the high pixel count of a classic fundus camera, but greatly improved contrast.
3. The relatively large aperture used in this approach improves sensitivity to slightly out of focus light. This could improve imaging of the optic disk and retinal features such as drusen that are displaced axially from the retinal pigment epithelium (RPE), and improve the ability to image a large field of view in the presence of myopia.

This BLFI imaging system can have several variants:
1. Separation of illumination and detection can be achieved either using a dielectric mirror or via a pupil splitting minor to selectively separate components of the light reflected from the eye and the illumination. Typically, a dielectric minor would be used for fluorescence imaging and pupil splitting for color imaging
2. Bright and dark images can be acquired either sequentially or simultaneously. The imaging can be using either de-scanned or non-de-scanned (imaged) detection. The distinction being in a de-scanned system, the same region of interest is used for different locations in the retina while in non-de-scanned or imaged detection there is a one to one correspondence between points on the retina and points on the detector array.
3. If a particular wavelength is required that is not available with LEDs, a laser could be substituted for the LEDs, but at the risk of increased speckle in the images.

It is clearly better to acquire both the bright and dark images simultaneously as otherwise any motion of the eye between acquisitions will lead to artifacts in the final image due to incorrect subtraction of the background Likewise, interlaced color imaging is preferred over sequential imaging of the full image in each color as motion during sequential imaging can lead to misalignment between colors in the final image.

De-scanning detection of the scanned beam simplifies the acquisition as the same detector elements are used repeatedly for each bright and dark frame. However, as the individual elements in the detector array are scanned across the retina, there cannot be motion of the scanner during any individual acquisition. This requires that the scanner steps between acquisitions and stops during the acquisition. A second issue is that light collected from the center of the aperture is likely more intense than the light collected from the edges of the aperture, leading to a spatial modulation in image brightness with a spatial period corresponding to the detector aperture size. For a homogeneous LED-illumination that problem is likely solvable either by illuminating an area of the retina that is slightly larger than the area that can be imaged through the collection aperture, or by overlapping the acquired regions during the reconstruction of the image to prevent slit edge effects.

It is an object of the present invention to improve image quality and signal of broad line fundus images or imaging methods. In one embodiment, this is achieved by further minimizing the overlap between illumination and detection paths and eliminating or reducing reflexes using different pupil splitting arrangements than what has been used in the prior art. In a second embodiment, an improvement is realized by minimizing or enabling easy removal of motion artifacts and background such as stray light signal using a step-scan illumination/detection approach. In another embodiment, image improvement is realized by designs directed towards minimizing reflexes in the system. This can be achieved dynamically during image acquisition by adjusting system parameters such as the tilt of the ophthalmic lens, or the illumination or collection widths.

It is a further object of the invention to disclose solutions to different challenges in BLFI imaging. In one embodiment, it is possible to adapt the field of view of the instrument by adding or replacing an optical component with optional changing of the pupil splitting configuration. In another embodiment, specific details of light sources for use in BLFI imaging are described. In another embodiment techniques for aligning the instrument are presented.

The various embodiments of the present invention can be applied to one or more variants of BLFI imaging systems which will be described in detail. Aspects of some of the variants are also considered inventive.

BRIEF DESCRIPTION OF THE DRAWINGS

FIG. 1 illustrates four different broad line fundus imaging system variants.

FIG. 2 illustrates combining of multiple LEDS into a single virtual LED source for use in broad line fundus imaging systems. FIG. 2a shows the side view while FIG. 2b shows the front view looking into the LED chip. FIG. 2c illustrates an additional LED combining scheme for 3 LEDs.

FIG. 3 illustrates two different light conditioning scenarios to make different light sources more suitable for use in broad line fundus imaging systems. FIG. 3a shows the combining of multiple color LEDs and FIG. 3b shows the conditioning that could be applied to a laser source to make it suitable for broad line fundus imaging.

FIG. 5 illustrates one strip or stripe image from a broad line fundus imaging system.

FIG. 6 illustrates the imaging relationship between the illumination aperture and the pupil plane for reduced vignetting.

FIGS. 8a, 8b, 8c, 8d and 8f illustrate a plurality of pupil splitting scenarios for fundus imaging systems as viewed at the pupil aperture.

FIG. 8e is a preferred pupil splitting scheme for broad line fundus imaging systems.

FIG. 12 illustrates the relationships between width of no-man's land, the illumination width and the eye length for an optical surface imaged behind the retina.

FIG. 13a illustrates a case where the pupil splitting between illumination and collection paths is complete in the dimension perpendicular to the pupil splitting looking along the line of illumination on the retina. The pupil splitting along the line of illumination leads to significant overlap as shown in FIG. 13b.

FIG. 14 illustrates possible pupil splitting schemes for small and large pupils.

DETAILED DESCRIPTION

BLFI Variants

Figure 1A:
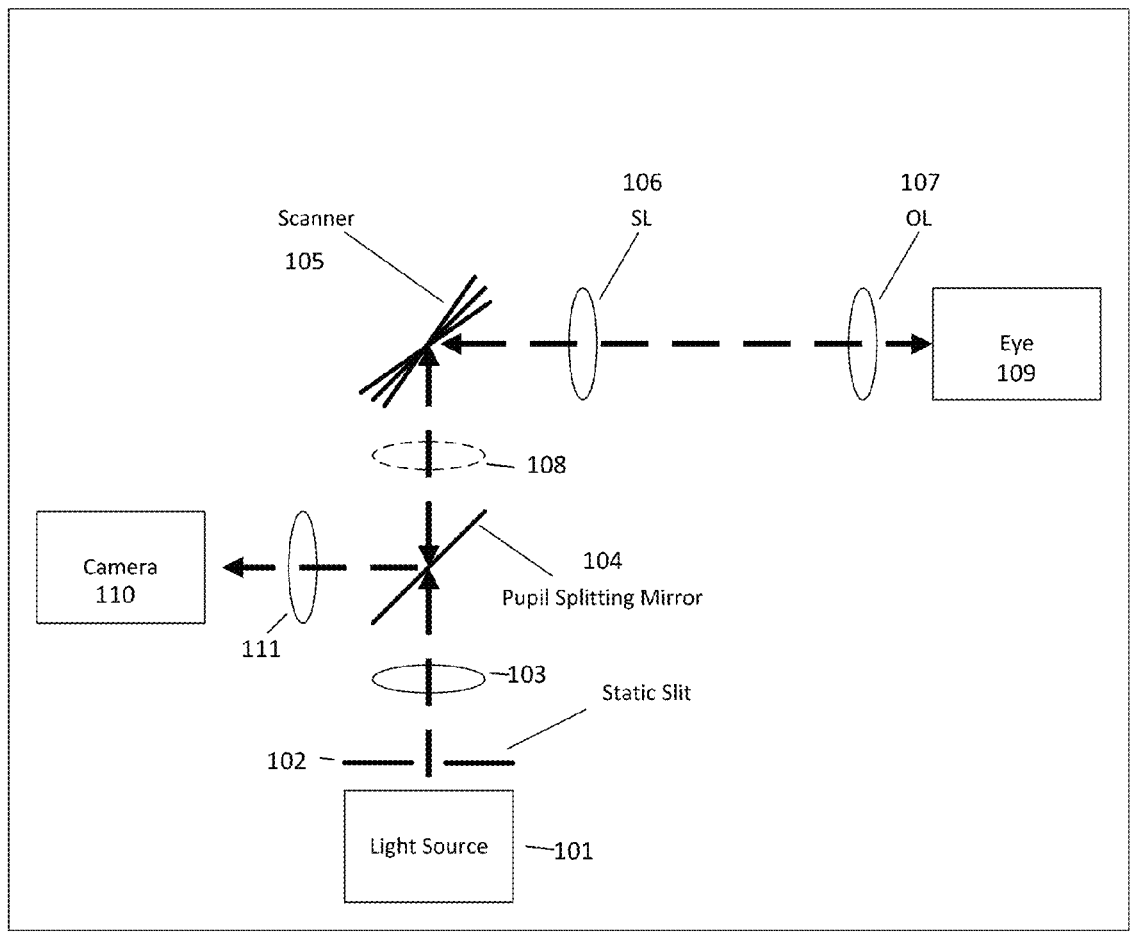
FIG. 1a illustrates the basic components of a de-scanned system.

Several variants of the broad line fundus imaging (BLFI) system are possible as illustrated in FIG. 1. FIG. 1a illustrates the basic components of a de-scanned system as is currently the preferred embodiment for a BLFI system. One or more light sources 101, preferably a multi-color LED system or a laser system in which the etendue has been suitably adjusted. In a preferred embodiment, light from red, green, blue, and IR LEDs are collimated and coupled together by dichroic mirrors and then focused in an optical microlens array or rod/taper. In a preferred embodiment using the microlens array, the LEDs are individually collimated and then the collimated LEDs are combined with a single lens to create a source with uniform illumination spatially and in the angular direction as is described in further detail below (FIG. 2). The IR light is typically used to generate an alignment image that can be displayed in real time to the user. The emission of the BLFI light source in the configuration shown in FIG 1a is much narrower in one direction than the other since when there is no unique (or full-field) mapping between the emission area of the light source and the retina, the emission area of the light source only needs to have the aspect ratio of the solid angle of detection that the illuminated region on the retina has and does not need to have the aspect ratio of the entire imaged area of the retina. An adjustable slit 102 is positioned in front of the light source to determine the illumination line width. This could also be established by the source independent of a slit or aperture. In the embodiment shown on FIG. 1a, this slit remains static during the imaging but can be adjusted to different widths to allow for different confocality levels and different applications either for a particular scan or during the scan for use in suppressing reflexes as described in further detail below. An objective lens 103 forms a pupil of the slit. The objective lens can be any one of state of the art lenses including but not limited to refractive, diffractive, reflective, or hybrid lenses/systems. The light passes through a pupil splitting minor 104 and is directed towards a scanner 105. It is desirable to bring the scanning plane and the pupil plane as near together as possible to reduce vignetting in the system as will be discussed in further detail below. Optional optics 108 may be included to manipulate the optical distance between the images of the two components. The main task of the pupil splitter is to combine and split the illumination and detection beams and to aid in the suppression of system reflexes. As described in further detail below, specific pupil splitting configurations are desired for different applications and optimized scanning. The scanner 105 could be a rotating galvo scanner or other types of scanners (i.e. piezo or voice coil). Depending on whether the pupil splitting is done before or after the scanner, the scanning could be broken into two steps wherein one scanner is in the illumination path and a separate scanner is in the detection path.

From the scanner, the light passes through one or more optics, in this case a scanning lens (SL) 106 and an ophthalmic or ocular lens (OL) 107, that allow for the pupil of the eye 109 to be imaged to an image pupil of the system. One possible configuration for these optics is a Keppler type telescope wherein the distance between the two lenses is selected to create an approximately telecentric intermediate fundus image (4-f configuration). The ophthalmic lens could be a single lens, an achromatic lens or an arrangement of different lenses. All lenses could be refractive, diffractive, reflective or hybrid as known to one skilled in the art. The focal length(s) of the ophthalmic lens, scan lens and the size and/or form of the pupil splitting and scanning minors could be different depending on the desired field of view (FOV), and so an arrangement in which multiple components can be switched in and out of the beam path, for example by using a flip in optic, a motorized wheel, or a detachable optical element, depending on the field of view can be envisioned. Since the field of view change results in a different beam size on the pupil, the pupil splitting can also be changed in conjunction with the change to the FOV. It is possible to have a 45°-60° field of view as is typical for fundus cameras. Higher fields of view (60°-120°) may be desired for a combination of the BLFI with other imaging modalities such as optical coherence tomography (OCT) as will be discussed in further detail below. The upper limit for the field of view will be determined by the accessible working distance in combination with the physiological conditions around the human eye. Because a typical human retina has a FOV of 140° horizontal and 80°-100° vertical, it may be desirable to have an asymmetrical field of view for the highest possible FOV on the system.

The light passes through the pupil of the eye and is directed towards the retinal surface. The scanner adjusts the location of the light on the retina or fundus such that a range of transverse locations on the eye are illuminated. Reflected or scattered light (or emitted light in the case of fluorescence imaging) is directed back along the same path as the illumination. While reflected light is typically used in the present document to describe the light returning from the eye, it is intended for reflected to include scattered light and it should be recognized that the words reflected and emitted could be used interchangeably depending on the desired imaging modality.

At the pupil splitting minor, the reflected light is separated from the illumination light and directed towards a camera 110. In a preferred embodiment the splitting between the illumination and the detection is achieved in a specific direction as described in further detail below. In particular, it is desirable that the etendue of the illumination beam is lower in that direction than in the orthogonal direction. The splitting can be designed such that the extent of illumination in the pupil can be narrower in the lower etendue direction and/or the angular distribution of the illumination light can be lower in the direction of the splitting as compared to the orthogonal direction. An objective lens 111 exists in the detection path to image the fundus to the camera. As is the case for objective lens 103, objective lens 111 could be any type of refractive, diffractive, reflective or hybrid lens as is known by one skilled in the art. Only a strip like region of the fundus will be illuminated and detected at once. Due to this, one part of the reflex and scattering interfering light from other optics in the system or the eye will be suppressed. The strongest reflex in the system is the corneal reflex. Optimized suppression of this reflex can be achieved in a number of ways as described in detail below. In a preferred embodiment, the illumination and detection zones are parallel to the area illuminated on the retina and separated by a "no-man's" zone as will be described in further detail below.

In the embodiment shown in FIG. 1a, the detection scheme is described as "de-scanned", in which the illumination light and light reflected by the fundus will both be deflected by the scanner (or the illumination and reflected light are deflected by two different scanners one time each as previously described). In this arrangement, the illumination slit and the detector are aligned fixed to each other and the fundus will be effectively "scanned" over the pixels of the camera. The camera can be operated in a global shutter configuration in which all pixels or detector elements are active during the acquisition. Descanning of the scanned beam simplifies the acquisition as the same detector elements or regions of interest (ROIs) are used repeatedly for each bright and dark frame. However, as the individual elements in the detector array are scanned across the retina, there cannot be motion of the scanner during any individual acquisition. To avoid the effects of motion, a time delayed integration (TDI) camera as described in German Patent Application No. DE 10 2011 053 880.1 hereby incorporated by reference can be used. In such a camera the acquired charges will be transferred to the next line of pixels when the light being scanned on the fundus has moved one pixel line as well. An alternative and preferred approach to the use of a TDI camera is to use a normal two dimensional spatial resolved camera and stop the scanner during the image integration in each broad line zone or strip. The scanner steps between acquisitions and stops during the acquisition as is discussed in further detail below.

Figure 1B:
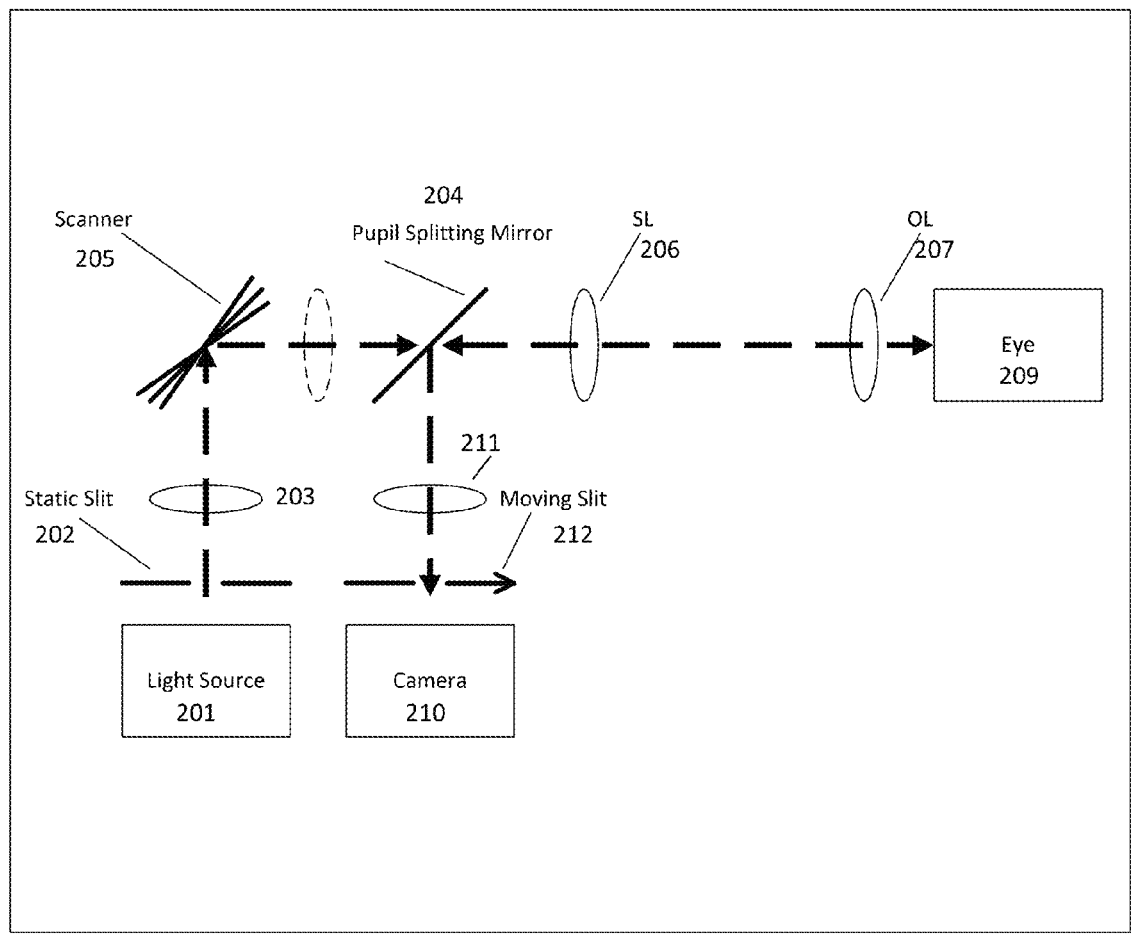
FIG. 1b illustrated a scanned or imaged detection configuration.

In a second variant of the BLFI technology that is illustrated in FIG. 1b, the detection is realized in a scanned or imaged configuration, such that during the time of acquisition, an entire image of the retina is built up on the camera with each position on the retina being uniquely mapped to a position on the camera and vice versa. In this type of configuration, only the illumination light is scanned and the light reflected (or emitted) from the eye is split at the pupil splitting minor 204 in front of the scanner 205 and directed towards a two dimensional position sensitive detector (camera 210). A moving slit or aperture is positioned in front of the camera and is moved synchronously with the scanner. In an alternative approach, the slit could be static and the slit and camera could be moved together to realize the same effect. Alternatively some sort of electronic aperturing or shuttering of the camera could be employed as is well known in the prior art (see for example Humphrey et al. U.S. Pat. No. 4,732,466 and Webb U.S. Pat. No. 5,028,802 hereby incorporated by reference). The lenses shown in FIG. 1b are of the same types and provide the same functions as the lenses in FIG. 1a. A "double rolling shutter" functionality is described in PCT Publication No. WO 2012/059236. In this configuration, at least two ROIs for the bright and dark images are designated and moved synchronously to the scanning of the illumination. This approach allows for optimized light efficiency and image quality.

Figure 1C:
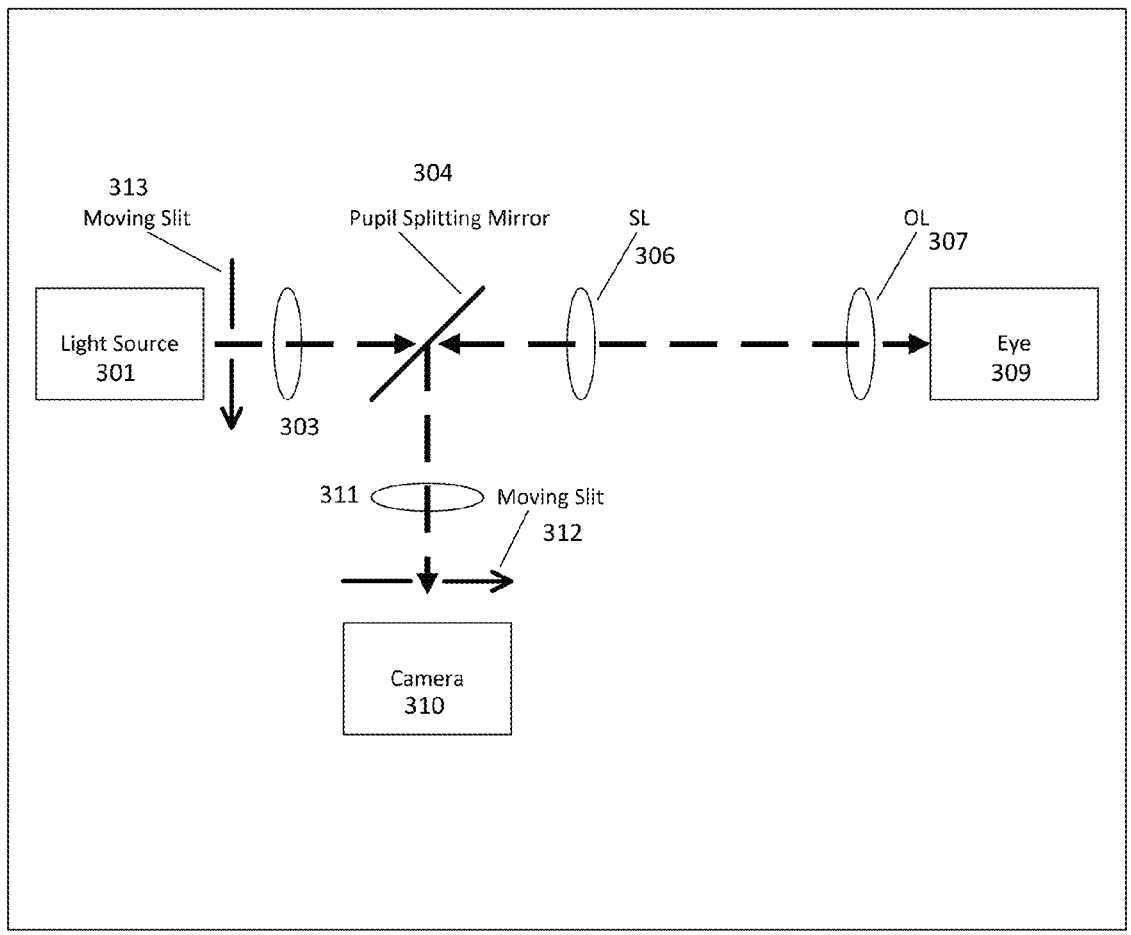
FIG. 1c illustrates an imaged or scanned detection arrangement but is realized without an actual scanner.

A third variant of the BLFI technology is illustrated in FIG. 1c. This configuration corresponds to an imaged or scanned detection arrangement but is realized without an actual scanner. Instead, a moving slit 312 in front of the camera 310 is moved synchronously with a moving slit 313 in front of the light source 301. Instead of a moving slit in front of the camera, a slit that is static with respect to the camera could be used and the camera and static slit could be moved together relative to the rest of the optical system. In this case, the emission area of the light source has the same aspect ratio as the image that is acquired. Similarly, instead of a moving slit in front of the light source, a slit that is static with respect to the source could be used and the light source and slit could be moved together relative to the rest of the optical system. In this case, the emission area of the light source can be narrower in one direction than in the other similar to the embodiment illustrated in FIG. 1a. Similar to the BLFI variant illustrated in FIG. 1b, each position in the retina is uniquely mapped to a position on the camera and vice versa. In addition, if the light source is static and the slit in front of it is moving, each position on the emission area of the light source is uniquely mapped to a position on the camera and vice versa. The width of the light source could also be a property of the source not requiring a slit.

Figure 1D:
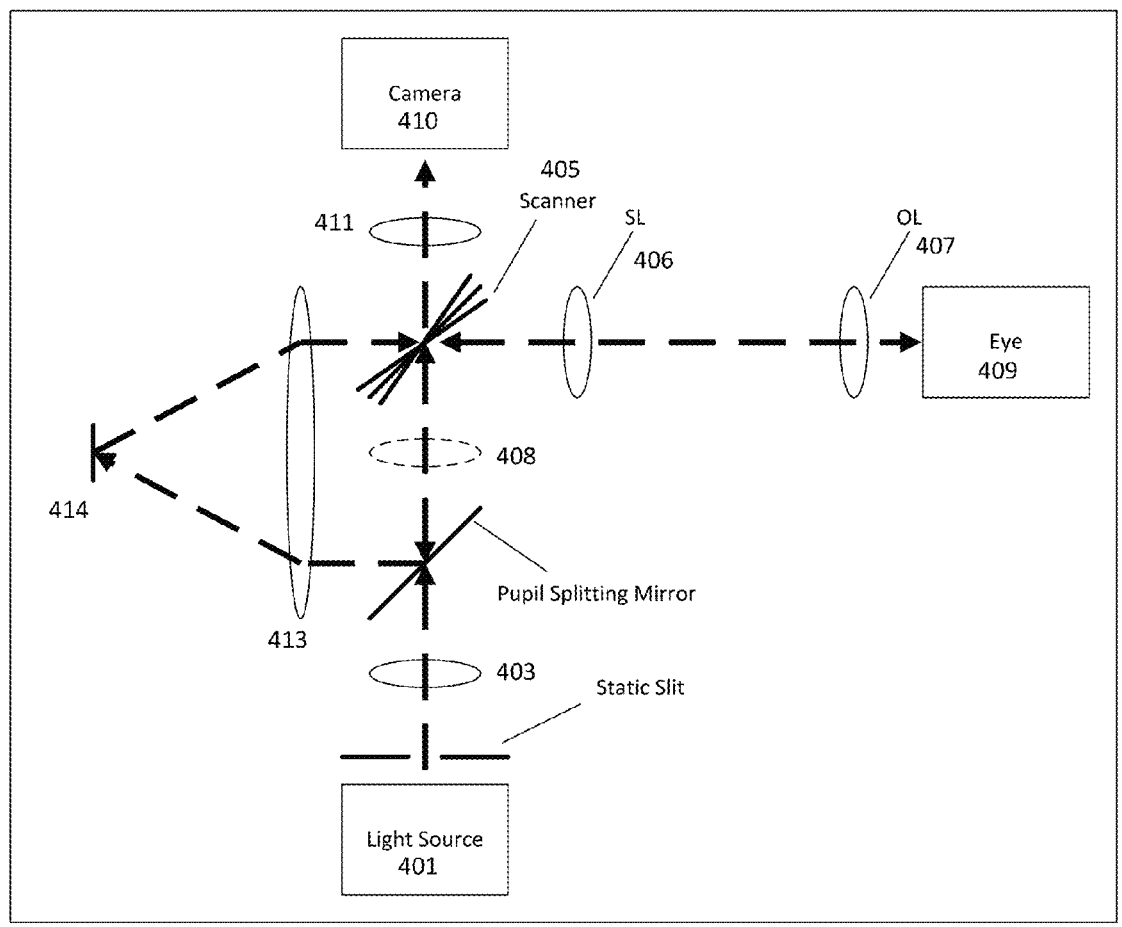
FIG. 1d shows a fourth variant in which both the front and back surfaces of the scanner are used in imaging.

FIG. 1d shows a fourth variant of BLFI technology in which the front surface of the scanner 405 scans the illumination light and the reflected light and the back surface of the scanner is used to scan the reflected light over the camera 410. Mirror 414 is used as the aperture equivalent to the moving slit in front of the camera in FIGS. 1b and 1c. A single lens 413 can be used to focus the beam onto minor 414 and redirect the light reflected from the mirror to the camera. The point at which light passes through lens 413 after reflection on minor 414 is at a different location than where it passes through the lens on the way to mirror 414. In other words, the entry point on lens 413 is off axis relative to the center of the lens. The emission area of the light source is much thinner in one direction than the other. Each position of the retina is uniquely mapped to a position on the camera and vice versa.

In all variants of the technology illustrated in FIG. 1, the camera can be connected to a processor and/or a display. The processing and displaying modules can be included with the instrument itself or on a dedicated processing and displaying unit, such as a personal computer, wherein data is passed from the camera to the processor over a cable or network including wireless networks. The display can include a user interface for displaying information to and receiving information from an instrument operator or user. For de-scanned systems in which the image is built up in parts, the processor is responsible for combining or mosaicking the multiplicity of images collected while stepping the scanner and combining them into a single image. In the processor, various steps are employed to generate the highest quality image as will be described in further detail below. In addition to the images of the area of interest, it is possible to collect dark images that can be subtracted to reduce or eliminate the effects of stray light or reflexes from optical surfaces in the instrument or other locations in the eye that may appear in the image. One aspect of the present invention includes improved techniques for background subtraction as will be described in further detail below.

Light Source Considerations

As previously mentioned, a multi-color LED illumination could be used for BLFI imaging. For example as illustrated in FIG. 3a, a blue, a green, a red and an infrared LED could be collimated with condenser lenses, coupled together with dichroic beam splitters and then focused with a lens into a mixing rod/taper/microlens array or other types of light homogenization device.

To realize a strip like illumination pattern in the exit plane of the homogenization device, a slit like aperture stop can be used. It is possible to establish motorized control of the slit width to adapt the BLFI to different confocality levels/applications. The homogenization device could additionally work as an etendue preserving toric field converter to adapt the light distribution efficiently in front of the aperture stop. A third function of the mixing device could be to adapt the telecentricity of the illumination light to that one of the following main objective lens.

To suppress the cornea reflex near a pupil plane, it could help to homogenize the light in the field and in the angular (far field) distribution. Therefore multilevel homogenization setups could be used. For example it would be possible to collimate the LEDs with compound parabolic concentrators or similar devices that work beside the collimation as a first level homogenization device. This basic setup is for acquiring color, FA and FAF images. To acquire ICG images or very high quality FA and FAF images, a laser source could be coupled in. Therefore in the front of the slit like aperture stop, a certain free distance could be intended with a motorized mirror to couple in any additional kind of light source that could be modularly exchanged. This is called a universal illumination port.

Because only a broad line in the fundus should be illuminated, an LED chip is needed which should be much longer than wide. Because only symmetric square chips are available, it is possible to use larger ones. Multichip LEDs that are elongated rectangular are one approach, or more preferred one could use square or rectangular chips over their diagonals.

For some wavelengths, for example 770 nm, which is necessary for ICG excitation, no high power large chip LEDs are available. For the typical etendue of a BLFI imaging system, at least 3 mm×1 mm LED chip size is necessary. Because only 1 mm LED chips are available for that color it is possible to realize a compound LED source with the etendue of a 3×1 mm chips.

A possible arrangement for a source consisting of seven LED chips is shown in FIG. 2a. Twelve chip and even higher numbers are possible with the same approach. FIG. 2a shows a sectional view, FIG. 2b shows the top view of the same arrangement in FIG. 2a. For the etendue required for BLFI, a special version of this source could be used with only 3 LED+ collimators arranged in a line as shown in FIG. 2(c). Each light emitting element (preferably LED) is separately collimated. The collimated beams are combined with a single lens. The resulting light beam has relatively uniform angular and spatial distributions.

It is further preferred to use laser as illumination source for special wavelength or special applications like ICG-angiography. But in contrast to state of the art LSLO (laser scanning line ophthalmoscopes), the laser light has to be converted by a non-etendue preserving element. The etendue of the laser should be enlarged from a diffraction limited beam to the etendue that could be transmitted of the BLFI. It is very important that the etendue of the so formed laser will fit quite well to the one of the setup, because larger etendues reduce the light efficiency of the setup and smaller etendues would enhance the exposure/hazard level in ophthalmoscopic applications.

Figure 8:
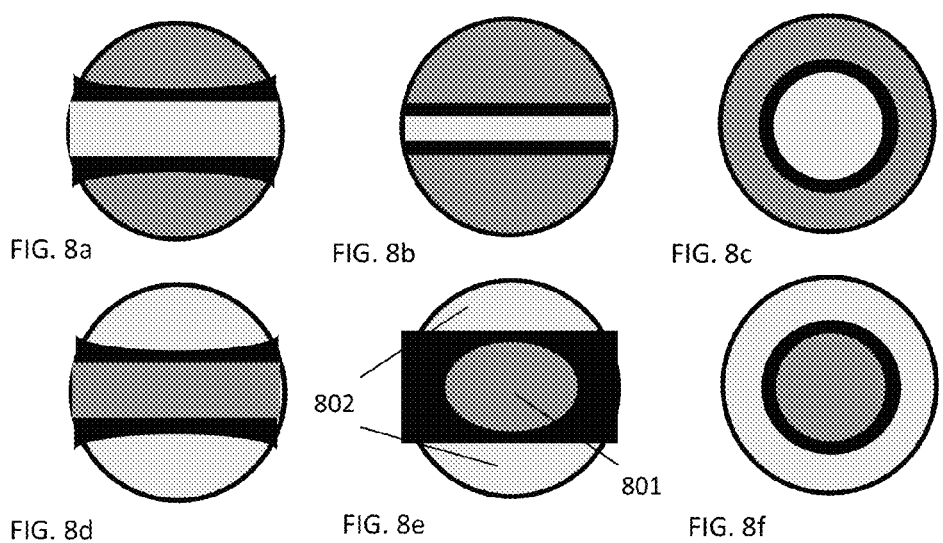
FIG. 8 illustrates various pupil splitting arrangements.

For the iris plane, the laser forms a very narrow line distribution too. Because this line will be stationary during the scanning it could be harmful to the iris tissue. For that reason it is necessary to enlarge the illumination line in the pupil plane from a few microns to at least 0.1-2 mm or more determined by the exact shape of the illumination zones shown in FIG. 8. For that purpose a scattering disc can be located in the illumination source directly in front of the slit like aperture stop to enlarge the etendue to safe levels (see FIG. 3b)). The scattering disc could have a motorized control distance to the aperture stop plane. While preserving the line width of the intensity distribution in the iris plane, you can control/adapt the line width in the retina plane and with it the confocality level with that distance.

Because of safety reasons it is mandatory to use scattering discs that have minimized hotspots in the near-, the far- and all intermediate fields. Due to this, only statistical microlens arrays or statistical scattering discs are preferred. Additionally it is preferred to use scattering devices that form a top-hat like far field distribution to homogeneous illuminate the retina in BLFI imaging.

In applications where speckle is a problem, the scattering disc can be rotated at a high speeds to average the speckle structures in the retina plane (and the harmful hotspots in all other planes). Because of the position of the scattering disc in front of the slit like aperture stop, the disc can control both the slit width in the iris for safety reasons and the width of the retina slit for adapting the confocality level to different application.

Multimodality Considerations

Figure 4:
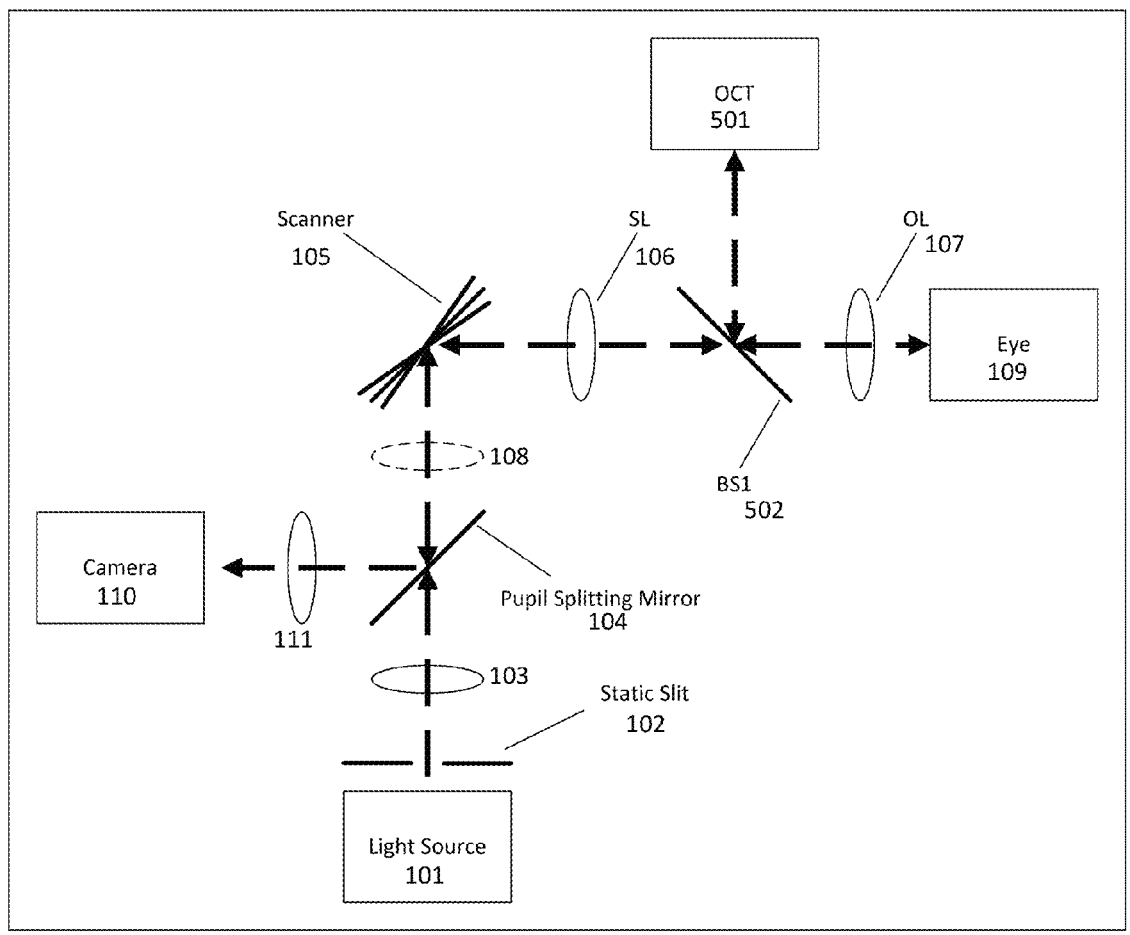
FIG. 4 illustrates a multimodality system combining a broad line fundus imaging system with an optical coherence tomography (OCT) system.

FIG. 4 shows the combination of the BLFI variant illustrated in FIG. 1a with an optical coherence tomography (OCT) system 501. One such system is described in detail in US Patent Publication No. 2007/0291277 hereby incorporated by reference. Any variant of OCT (time domain (TD), spectral domain (SD), swept-source (SS), full field (FF), or interferometric synthertic aperture microscopy (ISAM) could be combined with BLFI. The only addition to the BLFI beampath required is a beamsplitter BS1 502 used to reflect the OCT light and transmit the BLFI light. OCT systems typically operate in the infrared (800-1300 nm), so a filter capable of transmitting visible and reflected near IR would be desirable. In the configuration illustrated in FIG. 4, the OCT is introduced between the scanner and the eye between the scanning and ophthalmic lenses. The OCT system could be introduced on the other side of the scan lens and even on the other side of the scanner and the same scanner could be used for both imaging modalities. The BLFI system could be used to provide images for tracking as described in US Patent Publication No. 2006/0228011 and US Patent Publication No. 2012/0249956 hereby incorporated by reference. While OCT is shown here, BLFI can in general, be combined with other optical metrology systems to provide additional data or aid the operator in using the system optimally, potentially aiding in alignment, exposure time setting, fixation, etc.

Alignment and Focusing Considerations

Achieving optimal focusing of a de-scanned BLFI instrument can be accomplished using a live stream of IR images generating by only illuminating the eye with light from an IR LED. FIG. 5 shows an image generated from a de-scanned BLFI configuration as illustrated in FIG. 1a. Here, it is possible to view a bright area 1001 in the center of the image. This corresponds to the location of the illumination beam on the retina at that particular scanning step. The sharpness of the edge of the illumination area can be used to find the optimized focus of the system. This could be accomplished automatically by the instrument. Because the numerical aperture in the detection is much less that in the illumination, the illumination sharpness is much more depth dependent than the detection sharpness and so a very sensitive image sharpness parameter is created. If the illuminated area is near the fundus center, it is also possible to evaluate the focus position/edge sharpness along the illumination area and therefore the sharpness would depend on the field of view (FOV). In this case the optimal focus position for the whole FOV could be found. This is very important for large FOVs especially in the case of highly myopic eyes.

A method for aligning the instrument and thus especially aligning the pupil splitting near the cornea could be realized for all detection configurations (de-scanned, non-de-scanned, hybrid), by using an additional camera for capturing images of the pupil and iris of the patient. Such a camera, commonly referred to as an iris camera, has been realized in optical coherence tomography systems as described in US Patent Publication No. 2007/0291277 hereby incorporated by reference. For BLFI, an iris camera could be introduced between the scanning lens (SL) and the scanning plane in any one of the BLFI variants illustrated in FIG. 1. The system could find the optimal distance between the instrument and the eye by identifying an iris camera image with minimal vignetting. Alternatively, the overall sharpness of the image could be evaluated as the optimal separation between the instrument and the eye will result in the sharpest image. Both qualities could be evaluated automatically by the instrument using software algorithms in the processor. Alternatively, images could be provided to the user to manually focus the instrument.

Vignetting Considerations

Vignetting or reduction in brightness or saturation at the periphery compared to the image center in BLFI images can be minimized using several design considerations relating to the illumination and detection. For the illumination path, it is important that the effective pivot point of scanning is imaged to the pupil of the eye. If the illumination pupil aperture has structure in the non-scanned direction, this must be imaged to the pupil. It is not critical for structure in the illumination pupil aperture in the scanned direction to be imaged to pupil assuming the etendue of the light is highly limited in the scan direction. In addition, the far field illumination of the retina aperture must be at the pupil plane as illustrated in FIG. 6.

With regards to the collected light (reflected or emitted), the collection aperture must be imaged to the eye pupil assuming that the aperture has structure in the non-scanned direction. The pivot point of the collection scanning must be imaged to the eye pupil.

A solution that addresses these issues is to bring the scanner as near as possible to the pupil splitting plane and have the images at both locations be conjugated to the iris. This would reduce or eliminate vignetting in color as well as fluorescent images.

Background Subtraction Scenarios

It is an aspect of the present invention to improve image quality/signal of BLFI systems or methods by minimizing or enabling easy removal of motion artifacts and background/stray-light signal using a step-scan illumination/detection scheme and refined algorithms. Here the image post processing is explained in the de-scanned detection scheme for color imaging.

The scanner steps to the first position. A red, a green and a blue image or a color image will be acquired as fast as possible and then the scanner steps to the next position. This cycle will be repeated until the whole field of view (FOV) is detected. For every scan position and every color, a typical image will be acquired similar to the image shown in FIG. 5 for the case of IR illumination. The fundus is located in the middle of the image. On both sides there is a transition region. In this zone the intensity will decrease from the illuminated level to the background level.

On both sides of the transition zone a dark strip image with the same width as the illuminated bright strip image can be acquired. It is easier and also possible to only acquire a single side dark image. But, because of the dark image subtraction artifacts in vignetted systems, collecting dark images from both sides is preferred. The so detected stripe or strip images will be registered to compensate for motion artifacts between the two adjacent stripe images. Because the time between two neighboring stripes of one color is only a few milliseconds, the motion displacement is only on the order of a few pixels. Therefore, the transition zones could be used to compensate the motion displacement. It is preferred to extend the width of the illumination zone to have enough overlap without shading between the stripe images.

The so registered stripe images for one color can be merged together to one full FOV image. Because the image contains data from a much broader zone than the illuminated scanner steps, the dark image parts will overlap to the bright image parts of the next two stripes. The so overlapped image can be dissected into a bright and two dark images without interruptions and in a pixel correspondent way. The two dark images will be averaged and then subtracted from the bright image. The so processed image could show stripe like intensity variations. To compensate for them, a saturation adaption in the borders of the stripes can be performed.

An alternative solution would be to have a transition zone of at least half the bright stripe width. Then the transition zones on both sides of the bright stripe could be also merged to a "transition image" without interruptions and pixel correspondent to the bright and the dark images. The reconstructed image will then be calculated by adding the transition image and the bright image and subtracting both of the dark images taken on either side of the bright image. The basic idea behind this is that in the border of an illuminated stripe because of optical aberrations, defocus in combination with an extended retina thickness, a certain part of the illumination brightness will be transferred to the transition zones. So if the transition zones will be added to the bright image, all the transferred intensity will be corrected so the reconstructed image will show much less stripe intensity artifacts.

The subtraction of a dark image could correct all parasite light effects like scattering in the eye lens and auto fluorescence of the eye lens if they are not structured. But because the reflexes of the ophthalmic lens (OL) and scan lens (SL) are highly structured they will not be identical in the bright and dark images and therefore a dark image subtraction could cause additional artifacts in the final image. For this reason the OL and SL reflexes can be suppressed by the help of a "no eye image". The no eye image will be acquired in the same way described above but with a black cap in front of the ophthalmic lens so that the eye is blocked. The no eye images will be specific for every color and every focus position and could be acquired one time at the time of manufacture of the instrument or daily as part of an instrument initialization protocol. The no-eye image would then be stored in a data base. It is also possible but not preferred to acquire the no eyes images directly in front or after each patient image.

Before the image reconstruction, the no eye image will be subtracted from the patient image. To do so the unregistered stripe images with bright, dark and transition zones will be subtracted by the correspondent no eyes stripe images.

In the bright image there are typically two smaller regions close to the OL front side reflex and in the near of the optical nerve head where the image brightness is much higher than in the rest of the image. For the dark and no eye image subtractions, it is necessary that all images are not saturated. If camera sensors with a small dynamic range will be used, the signal to noise ratio could then be limited in the rest of the reconstructed image. To get better image quality it is preferred to realize high dynamic range (HDR) stripe images in the nerve head- and OL reflex regions. All HDR- methods known from the state of the art could be used therefore.

For all fluorescence images, the SNR in the reconstructed image is the most important quality feature. In fluorescence applications, the dark images contain no reflex light because of the wavelength shift between illumination and detection. So the dark images are mostly affected by auto fluorescence light of the eye lens and therefore the dark image only contains a small amount of structure. To get better SNR under these circumstances it is preferred to locally average the dark images to reduce the noise and to adapt the degree or range of averaging to the degree of structure.

Figure 7:
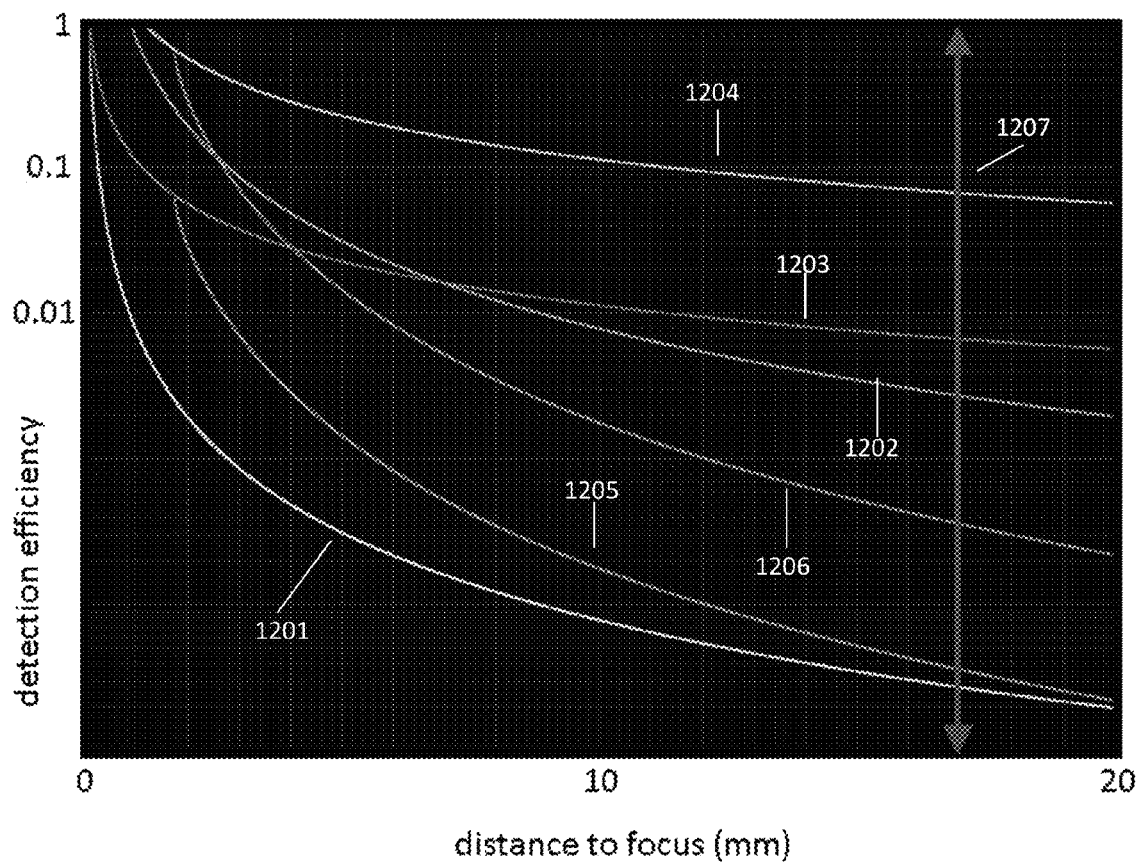
FIG. 7 illustrates depth discrimination functions corresponding to the part of light reflected in a plane at a certain distance to the focus (x-axis) that could be detected behind the confocal aperture stop for a plurality of optical imaging systems.

In the following section basic parameters for the optimization for the transition zone between bright- and dark image will be explained. FIG. 7 shows depth discrimination functions corresponding to the part of light reflected in a plane at a certain distance to the focus (x-axis) that could be detected behind the confocal aperture stop. For light that will be reflected in the focus region, the detection efficiency is 1 for every measurement principle. The detection efficiency will decrease if the distance to the focus is increased and the exact functionality is described by a specific depth discrimination function. All curves depend on the detection wavelength and the pupil size in the eye but could be qualitatively compared by the help of the diagram above.

The white curve 1201 in FIG. 7 shows the depth discrimination function of a confocal scanning laser ophthalmoscope with a closed pinhole. The detection efficiency will decrease quadraticaly with the distance to the focus. It has the strongest confocal suppression level for all focus distances compared to the other detection methods.

If the pinhole will be opened (to around 10airy) the curve will be changed to the blue one 1202. It has the same functionality but is scaled by a factor of 10 in the x-direction.

A line scanning laser ophthalmoscope with single line detection is shown in the red curve 1203. The function is around the square root of the white curve. That means for all distances the confocal level is much reduced.

The yellow curve 1204 shows a broad line scanner with a multi-line illumination and detection (around 10 lines). With regard to the functionality it is a 10 times scaled version of the red curve in the x-direction. The confocality level is much less than for the other functions. The green curve 105 is equivalent to the red one but with a dark line subtraction. The dark line has a certain distance to the bright line that could be controlled. For small out of focus distances the dark line will be dark and the subtraction will have no effect. Therefore for small out of focus distances, the red and the green curves are identical. Beginning with a certain distance to the focus the line image will be blurred so much that a part of the illumination brightness will illuminate the dark line too. Than a dark line subtraction affects the functionality of the curve as can be seen in a split of the green and red curve. For larger defocuses the depth discrimination with dark image subtraction is much stronger than for the line scanner without dark line subtraction.

The violet curve 1206 is a multi-line illumination and detection combined with a dark multi-line subtraction and shows the properties of a specific BLFI variant with background subtraction. It is characterized by a very small near out of focus suppression and a very strong far out of focus suppression compared to the other detection methods.

For an efficient detection of light back scattered by the retina or of fluorescence light from the retina, it is important to have a very small near out of focus discrimination. Because the retina has a certain thickness and the image curvature could be different to the retina curvature, a highly sensitive imaging of all light from the retina could only be realized with such a system of small near out of focus discrimination.

Scattering/fluorescence light from the eye lens or reflex light from the cornea have a much larger distance to the focus region marked by the red arrow 1207 in FIG. 7. To get a good contrast in the retinal images, it is important to strongly suppress these far out of focus signals. For an optimal system for retinal diagnostics, a combination of weak near out of focus suppression with a very strong far out of focus suppression is required. A confocal scanning laser opthalmoscope can only influence the depth discrimination function by opening the pinhole size. This will influence the near and far out of focus discrimination but not the ratio of both.

For BLFI it is possible to choose the number of pixel lines that will be illuminated and detected at one time and with it the near out of focus suppression. But with the distance between bright and dark images in pixel lines, it is possible to determine the point where the violet curve and the yellow curve will split and with it the far out of focus suppression of the violet curve. This basic property of a BLFI with dark image subtraction will give this very significant advantage of very sensitive and high contrast fundus imaging.

The distance between bright and dark images can be fixed to a typical patient as described by a population average or can be made variable with the help of an appropriate detector with selective line read out. Thus this distance can individually be adapted to each patient and application e.g. by one or several images taken in advance of the image finally used for diagnostics. So an individually optimized image is generated.

While the considerations above are made in the context of a descanning system using a stepwise scanning of the illumination, the considerations can also be applied to non-de-scanned systems and/or continuous scanning systems Pupil Splitting Considerations Another aspect of the present invention is to improve image quality/signal of BLFI systems or methods by further minimizing overlap between illumination and detection paths or reducing reflexes using a different pupil splitting arrangement than in the prior art. The reflexes from most optical surfaces can be eliminated by minimizing overlap between illumination and collection light at the optical surfaces. This is best accomplished by minimizing the etendue of the illumination and collection light in one dimension and then using pupil splitting to separate their optical paths in this dimension. Pupil splitting can be accomplished using a special arrangement of a splitting optical element e.g. a mirror. The basic task of the splitting minor is to combine/split the illumination- and the detection ray path of a broad line scanner in a way that the illuminating path does not overlap with the detection path in regions of the eye which show high reflectivity-like the cornea surface or have strong scattering/fluorescence structures like the natural lens. This is optimally achieved by a splitting minor leading to pupil separation as shown in FIG. 8*e*. In this figure the green area 801 indicates area of the detection path and yellow areas 802 are those used by the illumination path. The black area indicates a zone (here referred to as "no-mans-zone") which is not used by either the illumination or the detection path and might actually be blocked by special apertures in the illumination respective of the detection paths. The optimal illumination according to FIG. 8*e* is done at two caps of a circular disc, while the detection is done centrally covering an ellipsoid or in a preferred case, a circular(not shown) disc pattern, both being separated by a "no-mans-zone" with nearly rectangular outer shape. The design has been named "DOD" since the letters are representative to the splitting shapes. In addition this pupil separation pattern and the splitting optical element which realizes that pupil separation is oriented with its longer edge of the rectangular "no-mans-zone" and thus or equivalently with the base of the caps describing the illumination aperture parallel to the illumination slit generated at the retina.

It is important that in contrast to the embodiment disclosed in PCT Publication No. WO 2012/059236 which essentially resembles the arrangement illustrated in FIG. 8*b*, the illumination and the detection areas are reversed. Thus in the prior art, the images generated by using the peripheral regions of the aperture are more affected by aberrations of the cornea than the image of the slit, which is generated by the peripheral regions of the aperture in the disclosed invention. Second, the orientation of the "no-mans-zone" relative to the illuminated slit at the retina is not perpendicular as it is the case in the prior art. Thus the crossing of the detection path and the imaging path can be arranged to be outside the natural lens, minimizing the detection of scattered light.

In additional contrast to prior art designs considered in Muller US Patent Publication No. 2010/0128221, the pupil splitting arrangement illustrated in FIG. 8*e* shows two caps or hemispheres of a disc as illumination aperture. The advantage of the hemispheric apertures is that more light is used for illumination of the slit at the retina than with the ring or elipsoidial illuminations of the prior art. This is especially important when LEDs, which are limited in their output power are used for fluorescence applications. Further, prior art keeps silent related to a "no-mans-zone" and also to the orientation of the illumination aperture relative to the orientation of the illumination at the retina.

In general for BLFI, other pupil separation areas can be envisioned as shown in FIGS. 8*a*, 8*c*, and 8*d*.

In a further embodiment, the splitting optical element creating the illumination/detection aperture could be variable or exchangeable. This variation or exchange will allow for adaptation of the aperture to different corneas of different persons e.g having to different corneal curvatures or corneal aberrations or depending on the imaging modality used. E.g. for fluorescence imaging the "no-mans zone" can be made thinner or an aperture separation omitted altogether to allow detection of faint fluorescence light all over the aperture when a wavelength splitter or filter is used somewhere in the detection path.

Further descriptions of pupil splitting considerations will now be considered.

Figure 9:
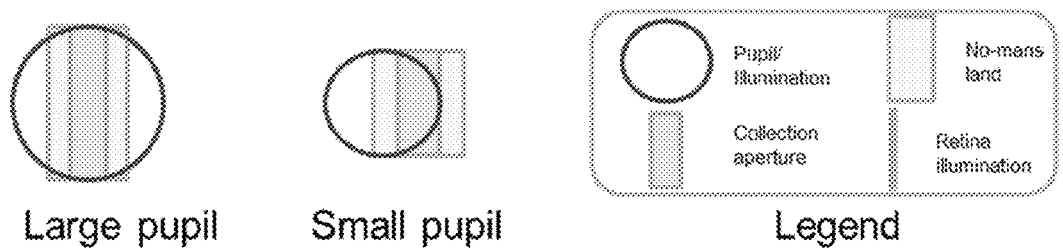
FIG. 9 illustrates relationships between pupil splitting and retina illumination directions for small and large pupil conditions in a particular pupil splitting arrangement.

If the illumination and collection on the pupil/cornea are displaced in the horizontal direction, we would need to minimize the etendue in this dimension by illuminating a vertical line on the retina. This illumination could be either in the form of two bands on opposite sides of the collection aperture or, for a smaller pupil, illumination on only one side as shown in FIG. 9.

Note that the pupil splitting and retina illlumination could both be rotated by 90 degrees if scanning vertically across the retina with a horizontal line was desired.

In addition to reducing or eliminating overlap between the illumination and collection at the optical surfaces, this approach also minimizes the overlap within the eye, greatly reducing issues with unwanted light from scattering or fluorescence. In the sections below we first analyze the overlap of the light within the eye, then extend the approach to consider the overlap of the light on optical surfaces of the imaging system outside of the eye.

Overlap between illumination and collection light within the eye

Figure 10:
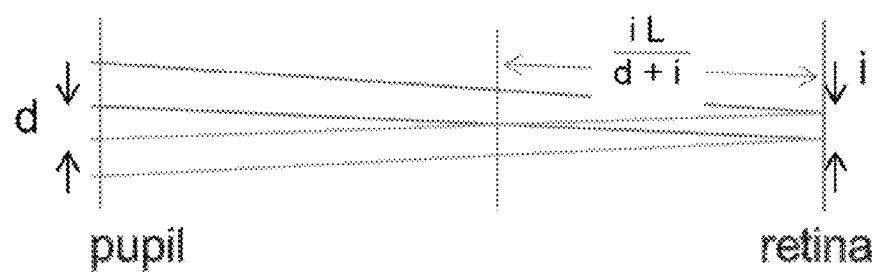
FIG. 10 illustrates the relationships between width of no-man's land, the illumination width and the eye length.

As shown in FIG. 10, the overlap between illumination and collection will extend over an axial distance from the retina toward the pupil of of I L/(i+d), where:
  d—Width of no-mans land (distance between illumination and collection on pupil)
  i—width of illumination on retina
  L—length of eye Minimizing overlap between illumination and collection in the eye is important for improving contrast as it reduces collection of unwanted scattered light from the eye. In addition, the regions of overlap and non-overlap are imaged throughout the optical system, so by making sure that no optical surfaces are in axial positions conjugate to this overlap region, one can eliminate issues with reflexes from the system.

Figure 11:
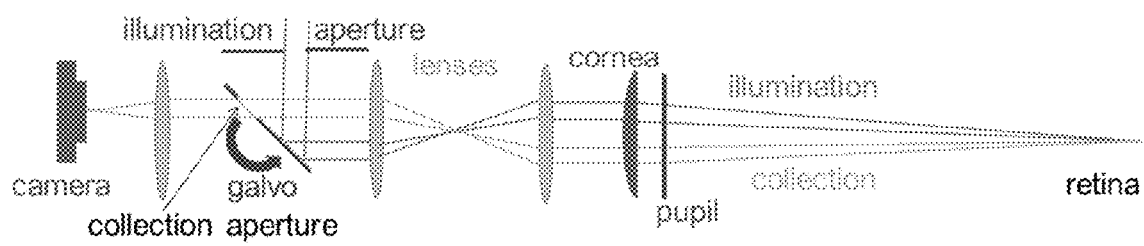
FIG. 11 illustrates a broad line fundus imaging system.

A complete optical diagram is shown in FIG. 11 to fully illustrate the point. The collection aperture and sensitive region on the camera together define the region between the green line where the light must come from to be detected. The illumination aperture and low etendue in the pupil splitting direction ensure that illumination light does not intercept these regions at any of the optics. Note that in this diagram, the separation between illumination and collection has been exaggerated. Typically, the pupil size is only a few millimeters, and therefore the illumination and collection light will be roughly a millimeter apart on the lenses.

One must also consider the issue of overlap between illumination and collection for optical surfaces imaged behind the retina. FIG. 12 shows just the critical rays from the top of the collection and bottom of the illumination shows that the region of overlap behind the retina extends a distance of i L/(d−i):

Here red denotes the bottom of the illumination aperture and orange denotes the top of the collection aperture. Note that this overlapping region will be imaged into the space from the imaged retinal plane behind the ophthalmic lens toward the cornea. As reflexes from the ophthalmic lens are of primary concern, the location of the ophthalmic lens relative to this imaged region is critical, and the ratio of i to d should be selected appropriately to make sure this region is short enough to avoid the ophthalmic lens.

The reason for the difference in overlap between in front of and behind the retina is that the side of the lines where light is an issue flips between in front of and behind the retina. Note that for all of the above examples, the overlap between illumination and collection is nearly complete in the dimension perpendicular to the pupil splitting along the line of illumination on the retina as shown in FIG. 13a. Also note that pupil splitting along the line of illumination leads to significant overlap as shown in FIG. 13b.

So far, we have assumed that the "pupil splitting" aperture is imaged to the pupil or cornea. However, for a de-scanned system, the splitting can be at any image plane from the pupil toward the imaging system. By placing the pupil splitting at the cornea, we have optimized the separation between illumination and collection at the cornea, at the expense of good splitting at the ophthalmic lens. By placing the pupil splitting roughly halfway between the cornea and ophthlamic lens, one should be able to have the beams nearly overlap at both the cornea and opthalmic lens thus reducing the region without overlap inside the eye, but extending the distance for which there is no overlap in front of the eye. Note that changing of the refractive error correction could impact the location of the pupil splitting.

Ophthalmic Lens Tilting

Another goal of the invention is to improve image quality/signal of BLFI systems by further minimizing reflexes such as those created by the ophthalmic lens (OL). One was this can be accomplished is by using a tiltable ophthalmic lens. For high myopic eyes the OL reflex will be concentrated/focused to the centre of the image. Due to this even small OL-reflectivities could result in very small and intensive reflexes. In such a situation it is nearly impossible to subtract the reflexes without any visible rest artifacts. The OL-reflex diameter is related to the defocus of the eye. It is not necessary to remove the whole reflex. If it is defocused enough it could be subtracted by the reflex subtraction.

The basic idea to suppress the OL reflex is to bring this reflex temporarily to other parts of the fundus image and to combine some of these images to a reflex free image. Because the most significant OL reflex is most critical if it is concentrated to a very small image region it is sufficient to shift it only a little bit with regard to the image content. This could be done with the help of a changed fixation target the patient will be asked to gaze to. It could be also done by using the motorized tilt and swivel functionality of the fundus camera to change the image contend behind the OL reflex. But most preferred it should be done with the help of a motorized ophthalmic lens tilt. Automated tilting could be realized in a number of ways including but not limited to: piezo elements, voice coil elements, cam shaft embodiments, linear solenoids, and galvanometers.

The basic imaging procedure is to take a normal image consisting of stripes than tilt—preferably perpendicular to the orientation of the illumination line on the retina—the OL by a few degrees and image all stripes in the center of the image that where effected by the OL reflexes in the first image again. A combination of these images will give a reflex free image. One could also acquire two partial images, which when combined could form the complete image. For instance, the first image could consist of the complete image minus the horizontal band containing the reflexes, and the second image could consist of this horizontal band with the reflexes shifted to a different vertical position.

The tilt angle will be determined in such a way that it will displace the OL reflex to have no reflex overlap with the not tilted image. In the case of strong myopic eyes where the intermediate image is located near the OL back side, the tilting angle will be determined to reflect out the OL back side reflex from the detection aperture. So in combination with a reflex subtraction the OL lens tilt could suppress the OL reflexes that no visible rest artifacts will remain.

Image Quality Considerations

For best imaging quality, we need to do several things:
1. Maximize optical efficiency by maximizing the illumination and collection areas on the pupil
2. Eliminate reflexes from optics and the eye (color and IR imaging) and scattering from the lens (all imaging)
3. Minimize focus/aberration issues by limiting collection aperture to within a small (roughly 1.5 mm diameter) circle As described in the pupil splitting design that maximizes optical efficiency while minimizing reflexes and scattering is shown in FIG. 9. However, the collection aperture needs to be limited for several reasons:
1. Optical aberrations of the eye
2. Increased depth of view to simplify focusing, particularly for novice users. Note—this requirement may be addressed by an autofocus function 3. Increased depth of view to address variations in the surface of the retina relative to best focus, particularly for large field of view imaging.
4. The optimum aperture in the absence of other constraints is circular, with a diameter somewhere between that of a standard non-myd fundus camera (diameter of 1.2 mm) and the FF-450. For ultra-wide field imaging, s the aperture diameter may need to be smaller to address the increased variation in best focus in the periphery.

Ideally, the optimum diameter circle can fit within the collection aperture area defined above. However, if it can't, then the collection aperture should be the overlap between such a circle, the pupil, and the rectangular aperture above. The resulting collection and illumination apertures for a small and large pupil are illustrated in FIG. 14.

Figure 15:
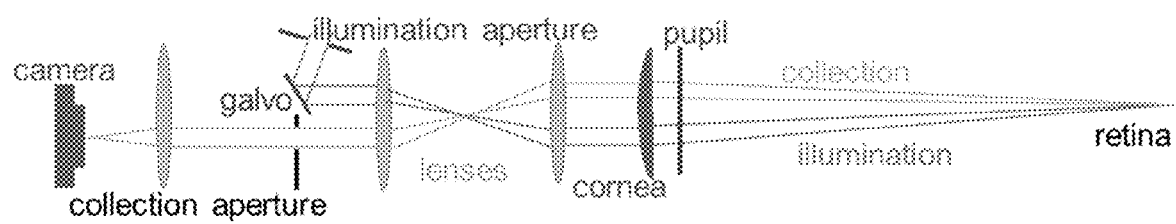
FIG. 15 illustrates a broad line fundus imaging system with a fixed collection aperture.

For instrument and operation simplicity, it is highly desirable to implement a single pupil splitting design that works for all sizes of pupils and for both fluorescence and color/IR imaging. Switching between different designs for different situations leads to the following issues:

1. There is a relatively uniform distribution of pupil sizes from small to large, and variations in pupil size during acquisition, so it will often not be clear which is the optimum setting to use
2. IR imaging is used for alignment during fluorescence imaging, therefore creating a conflict if the designs for IR and fluorescence imaging are different
3. The primary differences between small and large pupil designs are:
4. For large pupils, illumination on both sides of the collection aperture for increased optical efficiency
5. For small pupils, off-axis collection
6. The issue of off-axis collection is easily addressed as one can move the collection aperture toward the center of the pupil for larger pupils. The questions then become:
7. Is illumination on both sides of the collection aperture necessary for maximizing signal in the large pupil design?
8. Is the illumination of the iris an issue if the large pupil design is used for small pupils?
9. If all else is equal, the small pupil design is preferable from a design perspective, as illumination from only one side of the pupil simplifies the optical design, allowing an approach with a fixed collection aperture as shown in FIG. 15.

If one uses this design, the illumination should probably come from below so as this avoids use of the upper part of the pupil in with larger pupils, and this area is often covered by droopy eyelids in older people.

In addition, we need to consider whether the pupil splitting should be different for fluorescent imaging versus color/IR imaging as optical efficiency is of greater concern for fluorescence imaging.

The unique features of fluorescence imaging relative to color/IR imaging are:

1. Reflexes can be blocked by a dichroic minor, and therefore aren't an issue, allowing more flexibility in the illumination area
2. Fluorescence signal is generated at significantly lower efficiency (roughly a factor of 10 for FA and 100 for FAF) than scattering, reducing signal levels The similarities between fluorescence imaging and color/IR imaging are:

1. The collection aperture limitations to maintain quality focusing are roughly the same (there may be a slight difference due to larger spectral widths for the color imaging)
2. The need to avoid overlap between illumination and collection in the lens to maintain contrast is similar.

Assuming that it is possible to illuminate the entire pupil for fluorescence imaging as demonstrated with the BLFI, choosing to illuminate on only one side of the collection aperture will reduce the optical efficiency by a factor of roughly 2 to 6, depending on pupil size and whether off-axis collection is used.

Dynamic Illumination/Detection Width Adjustment

It is possible to eliminate the reflexes from the ophthalmic lens by limiting the illumination width on the retina and the collection width of the detection. This is not a viable option for the entire retinal image as it would require collection and mosaicking of too many lines of illumination, resulting in an overly long acquisition time.

However, the need for a reduced width retinal illumination is limited to the region where the reflexes are a concern, i.e. the central portion of the retina/ophthalmic lens. Therefore, if we can vary the illumination width during the scan, we should be able to eliminate the reflexes in the center of the image while only slightly increasing the acquisition time. For instance, if we needed to reduce the slit width by a factor of 3 over 1 tenth of the image, we would have to first order an acquisition time of 3*0.1+0.9=1.2, or a 20% increase in time. Note that this has no impact on total amount of illumination on the eye, integration time for any specific region, or amount of signal acquired for any portion of the eye.

As the illumination brightness and acquisition time for each individual slice is unchanged, the overall brightness of the image at each slice will remain the same. The illumination width could be defined in a variety of ways including but not limited to: passing light through a slit, reflecting light from a minor with a finite width, varying the extent of the light source. The collection width can be determined in a variety of ways including but not limited to: passing light through a slit, reflecting light from a mirror with a finite width, and active area of a detector. Either one or both of the illumination or collection widths could be varied dynamically.

Although various applications and embodiments that incorporate the teachings of the present invention have been shown and described in detail herein, those skilled in the art can readily devise other varied embodiments that still incorporate these teachings. While the description is focused largely on ophthalmic imaging, it is believed that some of the inventive concepts could have broader imaging applications.

The following references are hereby incorporated by reference:

PATENT LITERATURE

U.S. Pat. No. 3,547,512 Baer et al. "Optical apparatus providing focal-plane specific
U.S. Pat. No. 4,135,791 Govingnon et al. "Reduced glare scanner"
U.S. Pat. No. 4,732,466 Humphrey "Fundus camera"
U.S. Pat. No. 4,768,874 Webb et al. "Scanning optical apparatus and method"
U.S. Pat. No. 4,991,953 Webb et al. "Scanning laser vitreous camera"

U.S. Pat. No. 5,028,802 Webb et al. "Imaging apparatus and methods utilizing scannable microlaser source"

U.S. Pat. No. 5,177,511 Feuerstein et al. "Apparatus for producing images of an object and in particular for observing the rear portions of the eye"

US Patent Publication No. 2010/0128221 Muller et al. "Laser scanning digital camera with pupil periphery illumination and potential for multiply scattered light imaging"

US Patent Publication No. 2009/0244482 Elsner et al. "Laser scanning digital camera with simplified optics and potential for multiply scattered light imaging"

US Patent Publication No. 2004/0207811 Elsner "Device for digital retinal imaging"

PCT Publication No. WO 2012/059236 Bublitz et al. "Fundus camera with strip-shaped pupil division, and method for recording artifact-free, high resolution fundus images"

US Patent Publication No. 2007/0291277 Everett et al. "Spectral domain optical coherence tomography system"

US Patent Publication No. 2012/0249956 Iyer et al. "Systems and methods for efficiently obtaining measurements of the human eye using tracking"

US Patent Publication No. 2006/0228011 Everett et al. "Method and apparatus for measuring motion of a subject using a series of partial images from an imaging system"

German Patent Application No. DE 10 2011 053 880.1

NON-PATENT LITERATURE

Poher et al. "Improved sectioning in a slit scanning confocal microscope" Optics Letters 33(16), 1813-1815 2008.

What is claimed:

1. A method for collecting reduced artifact images of the fundus of the eye with a broad line fundus imaging (BLFI) system, said method comprising;
   scanning a beam of radiation over a range of transverse locations on the fundus of the eye, wherein the beam of radiation illuminates with a defined width on a region of the sample;
   collecting light returning from the eye in response to the illumination, wherein the region on the sample from which light is collected corresponds to the illumination area and has a defined collection width, wherein the width of the illumination light and/or the width of the collection area is adjusted during the scanning steps;
   generating an image from the collected light; and
   displaying or storing the image.

2. A method as recited in claim 1, wherein the illumination width is determined by one or more of the following: passing light through a slit, reflecting light from a mirror with a finite width, varying the extent of the light source.

3. A method as recited in claim 1, wherein the collection width is determined by one or more of the following: passing light through a slit, reflecting light from a mirror with a finite width, and active area of a detector.

4. A method as recited in claim 1, wherein the light is collected in a de-scanned configuration.

5. A method as recited in claim 1, wherein the light is collected in a non-de-scanned configuration.

6. A method for collecting reduced artifact images of the fundus of the eye with a broad line fundus imaging (BLFI) system, said method comprising:
   (a) scanning a beam of radiation over a range of transverse locations on the fundus of the eye;
   (b) collecting light returning from the eye;
   (c) scanning the beam of radiation over approximately the same range as when it was scanned over the eye;
   (d) collecting light reflected from the optical components in the system without collecting light returning from the eye;
   (e) subtracting the light collected at each transverse location in step d from the light collected at each transverse location in step b;
   (f) generating an image from the result of the subtraction; and
   (g) displaying or storing the image.

7. A method as recited in claim 6, wherein step d precedes step b.

8. A method as recited in claim 6, wherein step d is performed at the time the imaging system is manufactured.

9. A method as recited in claim 6, wherein step d is performed just before or after step b.

10. A method as recited in claim 6, wherein step d includes blocking light from reaching the eye.

11. A method as recited in claim 6, wherein step d includes acquiring an image when light is not present.

* * * * *

UNITED STATES PATENT AND TRADEMARK OFFICE
CERTIFICATE OF CORRECTION

PATENT NO. : 9,456,746 B2  
APPLICATION NO. : 14/207229  
DATED : October 4, 2016  
INVENTOR(S) : Daniel Bublitz et al.

It is certified that error appears in the above-identified patent and that said Letters Patent is hereby corrected as shown below:

On the Title Page

In item (72), in Column 1, in "Inventors", Lines 3-4, delete "Csaba Farkas, Pleasanton, CA (US);".

In item (72), in Column 1, in "Inventors", Lines 4-5, delete "Yue Qiu, Pleasanton, CA (US);".

In the Specification

In Column 2, Line 27, delete "ellipsiodal" and insert -- ellipsoidal --, therefor.

In Column 4, Line 18, delete "minor" and insert -- mirror --, therefor.

In Column 4, Line 20, delete "minor" and insert -- mirror --, therefor.

In Column 4, Line 36, after "background" insert -- . --.

In Column 5, Line 39, delete "imaging," and insert -- imaging. --, therefor.

In Column 6, Line 51, delete "minor" and insert -- mirror --, therefor.

In Column 7, Line 13, delete "minors" and insert -- mirrors --, therefor.

In Column 7, Line 45, delete "minor," and insert -- mirror, --, therefor.

In Column 8, Line 39, delete "minor" and insert -- mirror --, therefor.

In Column 9, Line 20, delete "minor" and insert -- mirror --, therefor.

In Column 9, Line 23, delete "minor" and insert -- mirror --, therefor.

Signed and Sealed this  
Twenty-seventh Day of March, 2018

Andrei Iancu  
*Director of the United States Patent and Trademark Office*

CERTIFICATE OF CORRECTION (continued)
U.S. Pat. No. 9,456,746 B2

In Column 11, Line 23, delete "synthertic" and insert -- synthetic --, therefor.

In Column 14, Line 28, delete "quadraticaly" and insert -- quadratically --, therefor.

In Column 15, Line 12, delete "opthalmoscope" and insert -- ophthalmoscope --, therefor.

In Column 15, Line 36, after "system" insert -- . --.

In Column 15, Line 50, delete "minor" and insert -- mirror --, therefor.

In Column 15, Line 56, delete "minor" and insert -- mirror --, therefor.

In Column 16, Line 29, delete "elipsoidial" and insert -- ellipsoidal --, therefor.

In Column 16, Line 57, delete "illlumination" and insert -- illumination --, therefor.

In Column 17, Line 5, delete "of of" and insert -- of --, therefor.

In Column 17, Line 62, delete "ophthlamic" and insert -- ophthalmic --, therefor.

In Column 17, Line 63, delete "opthalmic" and insert -- ophthalmic --, therefor.

In Column 19, Line 60, delete "minor," and insert -- mirror, --, therefor.

In Column 20, Line 39, delete "minor" and insert -- mirror --, therefor.